United States Patent
Juschka et al.

(10) Patent No.: US 7,558,378 B2
(45) Date of Patent: Jul. 7, 2009

(54) MULTILEAF COLLIMATOR

(75) Inventors: John Juschka, Eberbach (DE); Petra Juschka-Lenz, legal representative, Eberbach (DE); Johannes Reger, Erbendorf (DE); Rene Schramm, Whilhelmsfeld (DE); Steffen Seeber, Heidelberg (DE)

(73) Assignee: Siemens Aktiengesellschaft, Munich (DE)

( * ) Notice: Subject to any disclaimer, the term of this patent is extended or adjusted under 35 U.S.C. 154(b) by 37 days.

(21) Appl. No.: 11/899,348

(22) Filed: Sep. 4, 2007

(65) Prior Publication Data
US 2008/0063147 A1    Mar. 13, 2008

(30) Foreign Application Priority Data
Sep. 12, 2006    (DE) .................. 10 2006 042 726

(51) Int. Cl.
*G21K 1/04* (2006.01)
*A61N 5/10* (2006.01)

(52) U.S. Cl. .................................. 378/152; 378/65

(58) Field of Classification Search ......... 378/145–160, 378/65
See application file for complete search history.

(56) References Cited

U.S. PATENT DOCUMENTS

| | | | |
|---|---|---|---|
| 4,534,052 | A | 8/1985 | Milcamps |
| 4,868,843 | A | 9/1989 | Nunan |
| 5,012,506 | A | 4/1991 | Span et al. |
| 5,166,531 | A | 11/1992 | Huntzinger |
| 5,438,454 | A | 8/1995 | Ludewigt et al. |
| 5,889,834 | A | 3/1999 | Vilsmeier et al. |
| 6,711,237 | B1 | 3/2004 | Schlegel et al. |
| 7,106,831 | B2 * | 9/2006 | Li .......................... 378/152 |
| 2001/0053199 | A1 * | 12/2001 | Sundermann et al. ....... 378/147 |

FOREIGN PATENT DOCUMENTS

| | | |
|---|---|---|
| DE | 196 39 861 A1 | 4/1997 |
| DE | 199 05 823 | 6/2000 |
| GB | 2 362 080 | 11/2001 |
| WO | WO 00/46813 | 8/2000 |

OTHER PUBLICATIONS

German Office Action dated Jan. 11, 2008 for DE 10 2006 042 726.2-54 with English translation.
Abstract, Session YIS: Young Investigator's Symposium—Chicago Ballroom D/E, Medical Physics vol. 11 No. 3 May Jun. 1984, p. 390.

(Continued)

*Primary Examiner*—Irakli Kiknadze
(74) *Attorney, Agent, or Firm*—Brinks, Hofer, Gilson & Lione

(57) ABSTRACT

A multileaf collimator is provided. The multileaf collimator may be used for radiotherapy. The multileaf collimator may include a plurality of leaves that are adjustable along a displacement direction for the absorption of rays propagated along a direction of radiation, with opposing leaves relative to the displacement direction with front faces oriented toward each other being displaceable into a closed position. The multileaf collimator may also include a shielding-intensifying planar shape, which in closed position, is characterized by an at least partial overlapping of the front faces relative to the direction of radiation.

13 Claims, 3 Drawing Sheets

OTHER PUBLICATIONS

Sontag et al., Performance and beam characteristics of the Siemens Primus linear accelerator, Med. Phys. 26 (5), May 1999, pp. 734-736.

Zhu et al., Modeling the output ration in air for megavoltage photon beams, Med. Phys. 28 (6), Jun. 2001, pp. 925-937.

Sutherland et al., Sign Principles of Telecobalt Collimators, Med. Biol., 1977, vol. 22, No. 6, pp. 1189-1196.

Abstract, Session D: Radiation Therapy Posters: General Methods, Instrumentation, Quality Assurance—Grand Ballroom, Medical Physics, vol. 10, No. 4, Jul./Aug. 1983, p. 518.

* cited by examiner

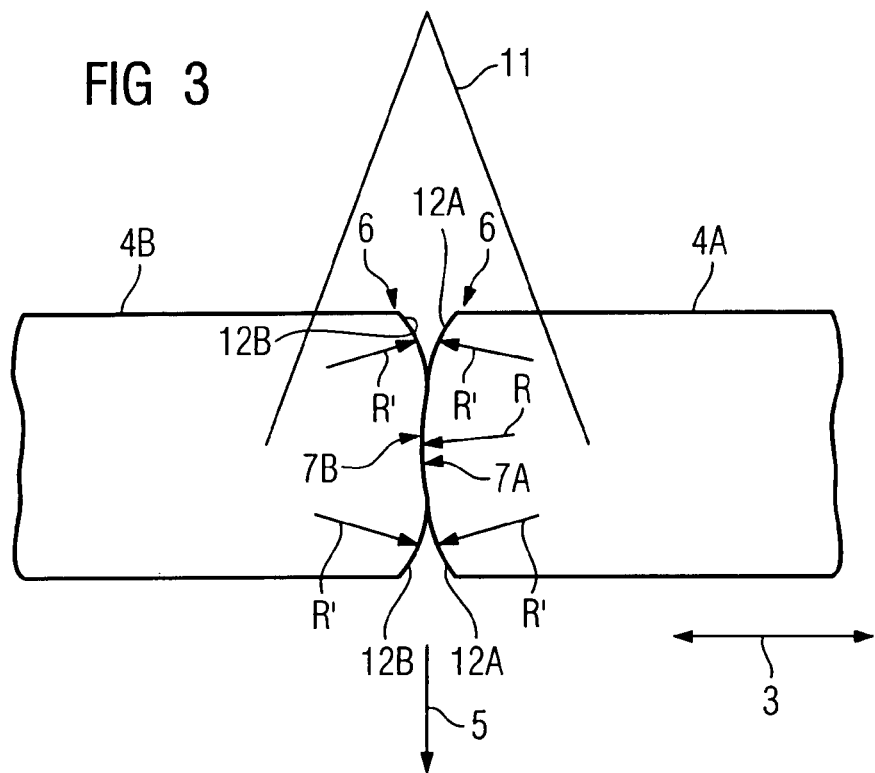
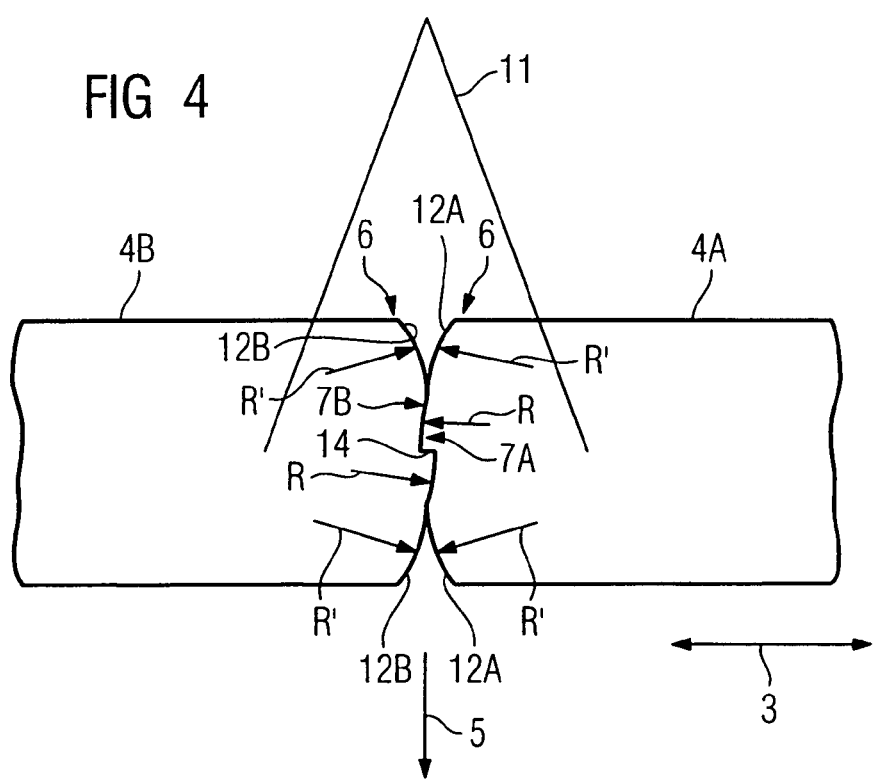

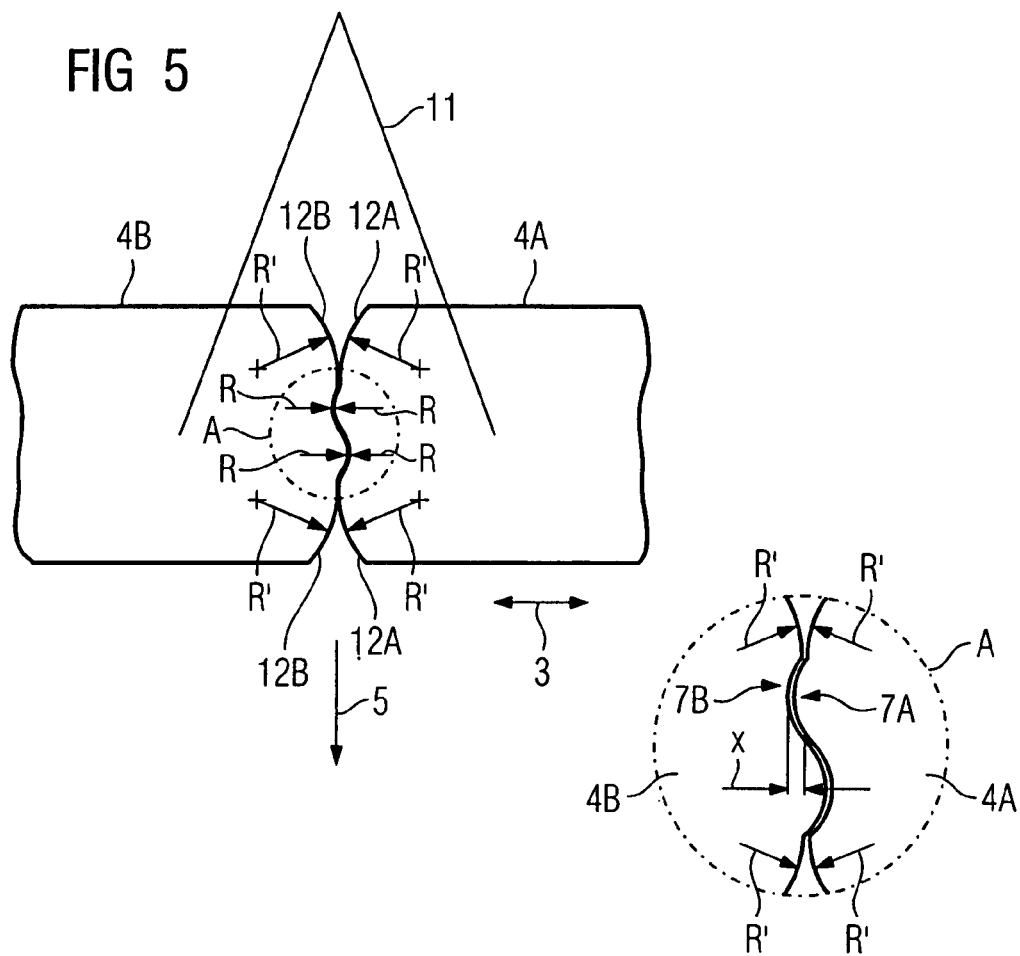
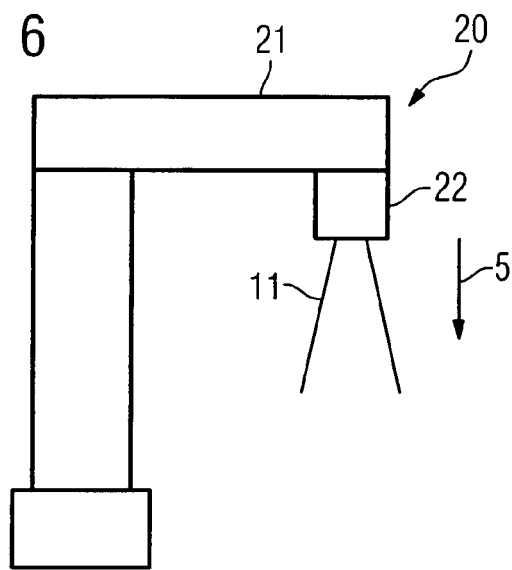

MULTILEAF COLLIMATOR

This application claims the benefit of DE 10 2006 042 726.2 filed Sep. 12, 2006, which is hereby incorporated by reference.

BACKGROUND

The present embodiments relate to a multileaf collimator.

Multileaf collimators are used for focusing radiation beams in radiotherapy devices, for example, with the therapeutic application of X-rays. Absorption may be used to focus high-energy electromagnetic radiation or corpuscular radiation, for example, in tumor therapy. A multileaf collimator is introduced into a beam path of a corresponding radiation source. This multileaf collimator includes a plurality of leaves made of an absorbent material, for example, tungsten. The leaves may be displaced in relation to each other. The thickness of the leaves in the direction of the beams is matched to the radiation energy for the application in question due to the finite penetration depth of the radiation in the absorbent material. DE 196 39 861 A1 and WO 00/46813 disclose a multileaf collimator of this kind. The leaves are arranged in two opposing parcels or groups in parallel or in a slightly semicircular configuration. The leaves can be moved with their front faces toward each other and away from each other in a displacement direction defined by the position of the collimator lying substantially in a plane orthogonal to the direction of radiation. The respective leaves, with opposing front faces, may be moved in opposite directions into a closed position. It is possible to establish an aperture with any cross section, outside of which the radiation is absorbed by the leaves. To establish irregular cross-section shapes, DE 196 39 861 A1 discloses collimators with narrow leaves. The area to be irradiated for a therapeutic application may be established precisely using the leaves.

Exposure to radiation, for example, during therapeutic applications, should be precisely defined with respect to the area and the time of the exposure. Side effects, such as scatter and extended field radiation into regions not intended for exposure, for example, in edge zones, may be limiting factors. To minimize side effects, the geometry of the leaves at the edges of which radiation may be scattered and the precision of the adjusting mechanism for the leaves, the desired and actual positions of which must correspond to a sufficient degree, should be considered. The degree of absorption of the leaves is also important in minimizing side effects. A collimator, as described above, may have undesirable partial radiation transmission, which is known as leakage, for example, penetrability. The front faces of the leaves, when they are in closed position, may have leakage. For example, radiation components may pass between the front faces.

SUMMARY

The present embodiments may obviate one or more of the limitations or drawbacks inherent in the related art. For example, in one embodiment, a multileaf collimator has reduced leakage in the region of the front faces.

In one embodiment, a radiotherapy device includes a plurality of leaves that are adjustable along a displacement direction for the absorption of radiation propagated along a direction of radiation, and opposing leaves relative to the displacement direction with front faces oriented toward each other being displaceable into a closed position.

In one embodiment, a multileaf collimator includes a shielding-intensifying leaf design, which includes partial overlapping of the front faces with respect to the direction of radiation in a closed position.

Partial overlapping in a closed position avoids a parallel alignment of the front faces to rays of the radiation beam emitted by the radiation source. The radiation beam may be propagated substantially slightly divergently fanned out along the direction of radiation. The radiation is forced to penetrate the absorbent material of the leaves. Direct radiation transmission between the front faces may be prevented. The front faces may not be in direct contact. A leaf adjusting mechanism with partially overlapping front faces has higher tolerances than conventional arrangements because conventional arrangements have front faces that are aligned parallel to radiation portions of the radiation beam so that, in a closed position, radiation transmission can only be reduced by direct contact of the front faces. Narrow tolerance limits are placed on the leaf adjusting mechanism and material fatigue takes place more quickly due to stresses in the leaves. The overlapping of the front faces provides relief for the adjusting mechanism with more effective radiation shielding and otherwise retention of the same functions. Radiation transmission may be reduced at the lateral edges of the leaves by a lateral inclination of the leaves.

The shielding-intensifying leaf design may include a front face shape with partial intermeshing. Partial intermeshing prevents unimpeded transmission of an incident ray from any direction. The ray has to penetrate the absorbent leaf material. Partial intermeshing includes intermeshing at least in one sub-area extending in the direction of radiation.

The front faces of the leaves include surface shapes that correspond to each other. For example, the shape of the front face of a leaf defines the shape of the front face of the leaf lying opposite the front face in closed position as a negative fitting shape.

In one embodiment, the front faces include smooth curves. A shielding-intensifying front-face geometry may include the smooth curves. The smooth curves do not impede the beam guidance of open leaves. Discontinuous surface structures, for example corners and steps, increases scatter effects.

In one embodiment, the edges of the leaves are rounded. The rounded edges reduce scatter effects of open leaves.

In one embodiment, a plurality of the front faces in the sub-areas includes sinusoidal surface profiles. The front faces in the sub-areas shield radiation in a closed position. The sinusoidal surface profile is a smoothly curved front-face profile.

In one embodiment, the amplitude of the sinusoidal surface profile of the front face shape lies in a range of approximately 0.1 mm to approximately 0.5 mm.

In one embodiment, the opposing, intermeshing front faces in closed position are curved correspondingly concavely and convexly toward each other.

In one embodiment, the radius of curvature of the concave/convex front faces lie within a range of approximately 200 mm to approximately 800 mm.

In one embodiment, the front faces in the sub-area have shoulders or steps. The front faces may extend the path of a beam through the leaf material and may be applied when using particularly high-energy radiation with relatively high penetration depths. Highly absorbent material may reduces scatter effects on the shoulders or steps.

In one embodiment, the width of the overlapping region of the front faces is in a range from approximately 0.1 mm to approximately 1 mm.

In one embodiment, the leaves are grouped in different planes. For example, in a closed position, leaves with opposing front faces may enclose an angle different from 180 degrees so that the leaves are not arranged in one and the same plane.

BRIEF DESCRIPTION OF THE DRAWINGS

FIG. 3 is a side view of two opposing leaves with one convex and with one rounded concave front face in a closed position, FIG. 4 is a side view of two opposing leaves with a shoulder introduced into the front faces in a closed position, FIG. 5 is a side view of two opposing leaves with sinusoidal front faces in closed position, and FIG. 6 is a radiotherapy device with a multileaf collimator.

DETAILED DESCRIPTION

Figure 1:
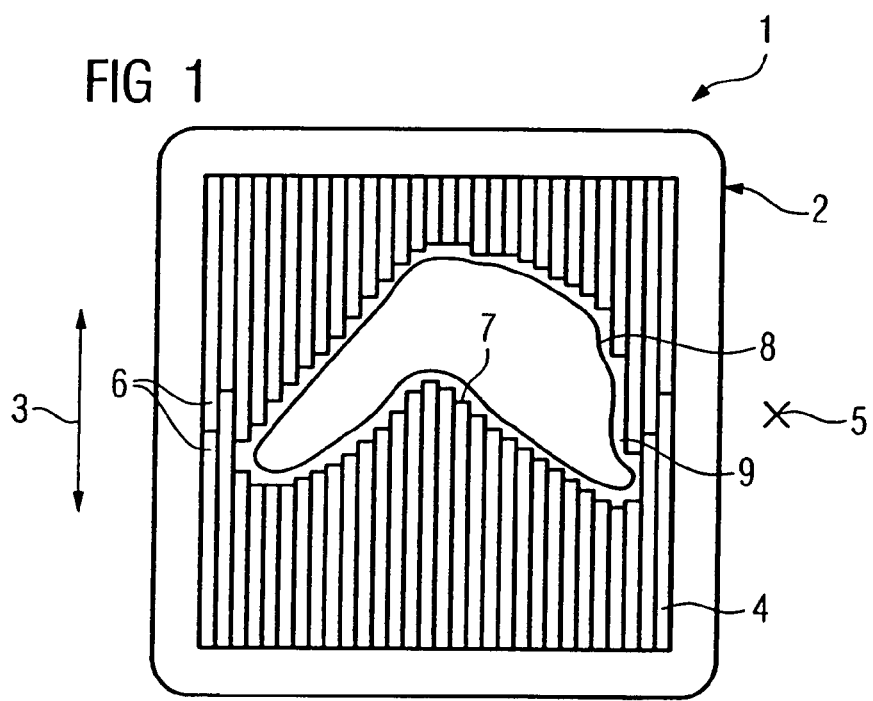
FIG. 1 illustrates one embodiment of a multileaf collimator in a plane perpendicular to the direction of radiation.

FIG. 1 is a schematic top view that shows one embodiment of a multileaf collimator 1. The multileaf collimator 1 includes a housing 2 and leaves 4 that may be adjusted along a displacement direction 3 using an adjusting mechanism. The housing 2 includes the adjusting mechanism. The leaves 4 absorb radiation from a radiation beam 11 from a radiation source 10 (see, e.g., FIG. 2). The radiation beam 11 has a main direction of propagation, which is substantially defined by a center axis of the normally slightly divergent radiation beam 11. This main direction of propagation is illustrated as the direction 5 of radiation which in this representation points perpendicularly into the image plane. The leaves 4 may be adjusted in opposite directions to each other as far as a closed position 6, in which the distance between the front faces 7 of leaves 4 is minimal. The adjustment of the leaves 4 enables an aperture to be specified for the radiation passing through the multileaf collimator 1 in the direction of radiation 5 so that the cross section of the radiation beam passing through corresponds to a predefined irradiation region 8 as far as edge zones 9.

Figure 2:
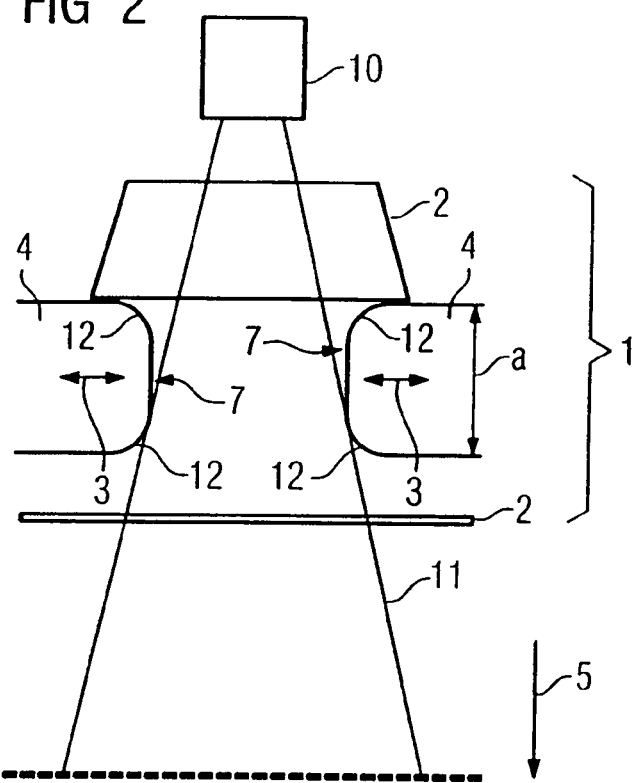
FIG. 2 is a side view of a radiation source with a conventional multileaf collimator depicting a beam path.

FIG. 2 is a schematic side view of the ray path through a conventional multileaf collimator 1. The multileaf collimator 1 is limited at both ends along the direction of radiation 5 by the housing 2. Leaves 4 may be moved along the displacement direction 3 with their front faces 7 facing each other. Leaves 4 may extend, for example, approximately 160 mm, in the direction of radiation 5. The radiation source 10 emits radiation in the form of a divergently fanned out radiation beam 11, the cross section of which is influenced by the setting of the leaves 4. The leaves 4 have rounded edges 12. The front faces 7 of the conventional multileaf collimator 1 are parallel to the direction of radiation 5. For example, the front faces 7 are parallel to each other.

In one embodiment, as shown in FIG. 3, two leaves of a multileaf collimator with opposing front faces may be in a closed position 6. The one leaf 4A comprises in the middle region a convexly curved front face 7A, for example, with a radius of curvature R of approximately 500 mm. The curvature merges continuously into the rounded edges 12A, which have a radius of curvature R' that corresponds to the radius of curvature R. The front face 7B of the opposing leaf 4B has a concave shape for an exact fit. The concave shape merges into the convex rounded edges 12B. The radii of curvature of the convex rounded edges 12B approximately correspond to those of the edges 12A, for example, approximately 500 mm. The overlapping range of the leaves 4A and 4B have a width of approximately 0.5 mm in the displacement direction 3. The divergent radiation beam 11 is propagated along the direction of radiation 5.

FIG. 4 is a side view of two leaves 4A and 4B with opposing front faces of a multileaf collimator in closed position 6. The shape of the front faces 7A and 7B is similar to that in FIG. 3. The front faces include a central shoulder 14 with a width of approximately 0.5 mm. The shape of the front faces, following the shoulder in the direction of radiation 5, mirrors the shape shown in FIG. 3. The width of the shoulder defines the width of the overlapping region in the displacement direction 3. The divergent radiation beam 11 propagates along the direction of radiation 5.

FIG. 5 is a side view of two leaves 4A and 4B with opposing front faces of a multileaf collimator in closed position 6. The front faces 7A and 7B include sinusoidal surface profiles, which each merge into convexly rounded edges 12A and 122B respectively. The sinusoidal surface radii of curvature R' are approximately of the same order of magnitude and, as shown in FIG. 3 and FIG. 4, are approximately 500 mm. The amplitude x of the sinus profile is approximately 0.2 mm. The width of the overlapping region in the displacement direction 3 corresponds to twice the amplitude. The divergent radiation beam 11 propagates along the direction of radiation 5.

FIG. 6 shows the schematic structure of a radiotherapy device 20 includes a central unit 21 and an irradiating head 22. A multileaf collimator 1, as described above, is introduced into the irradiating head 22 (see FIG. 2). The radiation beam 11 with a defined beam cross-section passing through the multileaf collimator emerges from the irradiating head 22 along the direction of radiation 5 and may be used for therapeutic purposes.

The invention claimed is:

1. A multileaf collimator for radiotherapy comprising:
a first plurality of leaves and a second plurality of leaves, which are adjustable along a displacement direction and operable to absorb rays propagated along a direction of radiation,
the first plurality of leaves opposing to the second plurality of leaves relative to the displacement direction with front faces oriented toward each other being displaceable into a closed position,
wherein, in the closed position, the front faces of opposing leaves overlap relative to the direction of radiation at least in a sub-area.

2. The multileaf collimator as claimed in claim 1, wherein the front faces of opposing leaves are intermeshed in the closed position.

3. The multileaf collimator as claimed in claim 2, wherein the intermeshed front faces comprise corresponding surface profiles.

4. The multileaf collimator as claimed in claim 2, wherein the front faces are correspondingly concavely and convexly toward each other for intermeshing.

5. The multileaf collimator as claimed in claim 4, wherein the front faces comprise a radius of curvature of approximately 200 mm to approximately 800 mm.

6. The multileaf collimator as claimed in claim 2, wherein the surface profile of the front faces comprises at least one shoulder.

7. The multileaf collimator as claimed in claim 1, wherein the front faces in the sub-area are smoothly curved.

8. The multileaf collimator as claimed in claim 7, wherein the front faces comprise rounded edges.

9. The multileaf collimator as claimed in claim 7, wherein the front faces comprise a sinusoidal front face shape.

10. The multileaf collimator as claimed in claim 9, wherein the sinusoidal front face shape comprises an amplitude of approximately 0.1 mm to approximately 0.5 mm.

11. The multileaf collimator as claimed in claim 1, wherein the front faces overlap in a region of approximately 0.1 mm to approximately 1 mm in the closed position.

12. The multileaf collimator as claimed in claim 1, wherein the leaves are grouped in different planes.

13. A radiotherapy device for shaping X-radiation, comprising:
   a multileaf collimator having at least two radiation absorbent leaves being adjustable in a direction substantially perpendicular to a direction of radiation, a first of the at least two leaves having a first front face and a second of the at least two leaves having a second front face,
   wherein the first and second front faces overlap each other in a closed position.

* * * * *